United States Patent [19]

Tapley

[11] Patent Number: 5,573,753
[45] Date of Patent: Nov. 12, 1996

[54] METHOD OF PREPARING SUNSCREENS

[75] Inventor: Carole A. M. Tapley, Stockton on Tees, Great Britain

[73] Assignees: Tioxide Specialties Limited; Tioxide House, both of United Kingdom

[21] Appl. No.: 953,265

[22] Filed: Sep. 30, 1992

[30] Foreign Application Priority Data

Oct. 4, 1991 [GB] United Kingdom ............ 9121153

[51] Int. Cl.$^6$ .................. A61K 7/42; A61K 7/40; A61K 7/021; A61K 7/025
[52] U.S. Cl. .................. 424/59; 424/60; 424/63; 424/64; 514/937; 514/938
[58] Field of Search .................... 424/59

[56] References Cited

U.S. PATENT DOCUMENTS

| | | | |
|---|---|---|---|
| Re. 27,818 | 11/1973 | Werner | 106/436 |
| 2,296,636 | 9/1942 | Hanahan | 106/294 |
| 2,387,534 | 10/1945 | Seidel | 106/300 |
| 2,885,366 | 5/1959 | Iler | 106/300 |
| 3,409,560 | 11/1968 | Faust et al. | 106/300 |
| 3,410,708 | 11/1968 | Mcginnis | 106/300 |
| 3,437,502 | 4/1969 | Werner | 106/300 |
| 3,579,310 | 5/1971 | Lewis et al. | 106/300 |
| 3,591,398 | 6/1971 | Angerman | 106/300 |
| 3,728,443 | 4/1973 | Berisford et al. | 106/300 |
| 3,907,581 | 9/1975 | Willcox | 106/300 |
| 3,923,968 | 12/1975 | Basque et al. | 106/300 |
| 3,928,057 | 12/1975 | Decolibus | 106/300 |
| 3,954,496 | 5/1976 | Batzar | 106/300 |
| 4,075,031 | 2/1978 | Allen | 106/300 |
| 4,199,370 | 4/1980 | Brand | 106/300 |
| 4,857,305 | 8/1989 | Bernhardt et al. | 424/59 |
| 4,882,143 | 11/1989 | Kadokura et al. | 424/59 |
| 4,917,883 | 4/1990 | Strobridge | 424/59 |
| 4,923,518 | 5/1990 | Brand et al. | 106/300 |
| 4,940,574 | 7/1990 | Kaplan | 424/59 |
| 5,000,937 | 3/1991 | Grollier et al. | 424/60 |
| 5,028,417 | 7/1991 | Bhat et al. | 424/59 |

FOREIGN PATENT DOCUMENTS

| | | | |
|---|---|---|---|
| 0073340 | 7/1982 | European Pat. Off. | 106/300 |
| 0214308 | 3/1986 | European Pat. Off. | 106/300 |
| 0433086 | 6/1991 | European Pat. Off. | |
| 2740561 | 3/1978 | Germany | 106/300 |
| 49-000450 | 1/1974 | Japan | 424/59 |
| 52-072833 | 6/1977 | Japan | 106/300 |
| 53-124627 | 10/1978 | Japan | 106/300 |
| 54-073139 | 6/1979 | Japan | 106/300 |
| 55-154317 | 12/1980 | Japan | 424/59 |
| 58-043912 | 3/1983 | Japan | 424/59 |
| 58-062106 | 4/1983 | Japan | 424/59 |
| 59-015885 | 4/1984 | Japan | 424/59 |
| 57-067681 | 4/1984 | Japan | 424/59 |
| 59-062517 | 4/1984 | Japan | 424/59 |
| 59-098009 | 6/1984 | Japan | 424/59 |
| 59-172415 | 9/1984 | Japan | 424/59 |
| 59-223231 | 12/1984 | Japan | 424/59 |
| 60-186418 | 9/1985 | Japan | 424/59 |
| 62-260716 | 11/1985 | Japan | 424/59 |
| 60-231607 | 11/1985 | Japan | 424/59 |
| 60-255713 | 12/1985 | Japan | 424/59 |
| 61-037711 | 2/1986 | Japan | 424/59 |
| 61-097133 | 5/1986 | Japan | 424/59 |
| 61-215216 | 9/1986 | Japan | 424/59 |
| 62-040292 | 8/1987 | Japan | 424/59 |
| 63-072620 | 4/1988 | Japan | 424/59 |
| 63-132821 | 6/1988 | Japan | 424/59 |
| 2212414 | 8/1990 | Japan | 424/59 |
| 2289506 | 11/1990 | Japan | 424/59 |
| 3134069 | 6/1991 | Japan | 424/59 |
| 3183620 | 8/1991 | Japan | 424/59 |
| 3199121 | 8/1991 | Japan | 106/436 |
| 458535 | 3/1975 | U.S.S.R. | 424/59 |
| 1109369 | 12/1965 | United Kingdom | 106/300 |
| 1256341 | 12/1971 | United Kingdom | 424/59 |
| 1387281 | 3/1975 | United Kingdom | 424/59 |
| 1541621 | 5/1976 | United Kingdom | 106/300 |
| 1479988 | 7/1977 | United Kingdom | 424/59 |
| 1500600 | 2/1978 | United Kingdom | 424/59 |
| 2108097 | 9/1982 | United Kingdom | 106/300 |
| 2184356 | 6/1987 | United Kingdom | 424/59 |
| 2205088 | 5/1988 | United Kingdom | 106/300 |
| 2206339 | 1/1989 | United Kingdom | 424/59 |
| 2226018 | 11/1989 | United Kingdom | 106/300 |
| WO9213517 | 8/1992 | WIPO | 424/59 |

*Primary Examiner*—Shelley A. Dodson
*Attorney, Agent, or Firm*—Baker & Botts, L.L.P.

[57] ABSTRACT

A method of preparing sunscreens in which a dispersion of zinc oxide particles in an oil is formed by milling in the presence of a particulate grinding medium and mixed with cosmetically acceptable materials is claimed. The particles of zinc oxide have an average size of from 0.005 to 0.15 micron and the dispersion is substantially transparent to visible light but with an extinction coefficient at 308 nm (E(308)) and at 360 nm (E(360)) of at least 9 liters per gram per centimeter. The ratio E(360):E(308) is in the range 0.75:1 to 1.5:1. In a preferred method a mixed dispersion containing titanium dioxide and zinc oxide, having E(308) at least 15 liters per gram per centimeter, E(360) at least 10 liters per gram per centimeter and the ratio E(360):E(308) in the range 0.3:1 to 1.5:1 is used. The mixed dispersion is also claimed. The sunscreens prepared have a good balance of absorption for UVA and UVB radiation and better SPF values than those prepared from titanium dioxide and/or zinc oxide powders.

35 Claims, No Drawings

METHOD OF PREPARING SUNSCREENS

This invention relates to a method of preparing sunscreens and in particular to a method of preparing sunscreens containing a dispersion of zinc oxide.

The general increase in numbers of people enjoying leisure activities outdoors and increasing their exposure to sunlight and an increasing awareness of the health problems associated with such exposure have led to a demand for efficient and effective sunscreen preparations. It is now widely accepted that an ideal sunscreen is one which can provide protection from both UVB radiation (wavelengths 290–320 nm) and UVA radiation (wavelengths 320–400 nm).

It is an object of this invention to provide an efficient method of preparing a sunscreen which provides a balanced protection from UVA and UVB radiation.

According to the invention a method for the preparation of a sunscreen comprises milling particulate zinc oxide in an oil in the presence of a particulate grinding medium and an organic dispersing agent for said zinc oxide in said oil to form a dispersion, continuing said milling for a period of time such that the particulate zinc oxide has an average size of from 0.005 to 0.15 micron and that the dispersion is substantially transparent to visible light and has an absorbance for ultraviolet light such that the extinction coefficient (E(308)) at a wavelength of 308 nm is at least 9 liters per gram per centimeter, the extinction coefficient (E(360)) at a wavelength of 360 nm is at least 9 liters per gram per centimeter and the ratio E(360):E(308) is in the range 0.75:1 to 1.5:1, separating the particulate grinding medium from the dispersion and mixing the dispersion with one or more cosmetically acceptable materials.

In a preferred method of the invention a dispersion containing a mixture of zinc oxide and titanium dioxide is prepared.

According to the preferred embodiment of the invention a method for the preparation of a sunscreen comprises milling particulate zinc oxide and particulate titanium dioxide in oil in the presence of a particulate grinding medium and an organic dispersing agent for said zinc oxide in said oil and an organic dispersing agent for said titanium dioxide in said oil, continuing said milling for a period of time such that the particulate zinc oxide and the particulate titanium dioxide each have an average size of from 0.005 to 0.15 micron, forming a mixed oxide dispersion, said dispersion being substantially transparent to visible light and having an absorbance for ultraviolet light such that the extinction coefficient (E(308)) at a wavelength of 308 nm is at least 15 liters per gram per centimeter, the extinction coefficient (E(360)) at a wavelength of 360 nm is at least 10 liters per gram per centimeter and the ratio E(360):E(308) is in the range 0.3:1 to 1.5:1, separating the particulate grinding medium from the dispersion and mixing the dispersion with one or more cosmetically acceptable materials.

It is to be understood that the mixed oxide dispersion formed in the above preferred method can be produced by co-milling the zinc oxide and titanium dioxide or by separately milling the two oxides and subsequently blending the dispersions thereby produced. When the oxides are milled separately then the particulate grinding medium may be removed from one or both of the dispersions before they are blended together.

The sunscreens prepared according to the methods of the invention provide protection from both UVA and UVB radiation but the use of titanium dioxide allows more flexibility in the balance of the UVA and UVB absorption than is possible with zinc oxide alone.

The amount of zinc oxide or zinc oxide and titanium dioxide used depends upon the type of sunscreen prepared and its desired sunscreening efficacy. However, it is desirable to obtain a high solids content in the dispersion since this enables a wide range of final products to be produced from the dispersion.

A dispersion of zinc oxide containing greater than 30 per cent by weight zinc oxide and suitable for use in the method of this invention is disclosed in our co-pending application.

The preferred method utilises a mixed oxide dispersion and a novel dispersion for use in the preferred method comprises an oil, particles of zinc oxide having an average size of from 0.005 to 0.15 micron, particles of titanium dioxide having an average size of from 0.005 to 0.15 micron and an organic dispersing agent for said particles in said oil, the amounts of said particles being such that the dispersion has a total solids content of greater than 30 per cent by weight and said dispersion being substantially transparent to visible light and having an absorbance for ultraviolet light such that the extinction coefficient (E(308)) at a wavelength of 308 nm is at least 15 liters per gram per centimeter, the extinction coefficient (E(360)) at a wavelength of 360 nm is at least 10 liters per gram per centimeter and the ratio E(360):E(308) is in the range 0.3:1 to 1.5:1.

Preferably this mixed oxide dispersion has a total solids content greater than 40% by weight since this high solids content allows flexibility in formulating the final sunscreen.

The particulate zinc oxide and, in the preferred embodiment, the particulate titanium dioxide are milled in the oil until the particles have an average size of from 0.005 to 0.15 micron and where the particles are substantially spherical then this size will be taken to represent the diameter. However since the invention also encompasses the use of non-spherical particles then in such cases the size refers to the largest dimension. Preferably the particles of zinc oxide have an average size within the range 0.01 to 0.1 micron and most preferably within the range 0.03 to 0.07 micron when they are substantially spherical in shape. Preferably the particles of titanium dioxide have an average size within the range 0.01 to 0.03 micron when they are substantially spherical in shape. For particles having an acicular shape then the average largest dimension preferably is within the range 0.05 to 0.12 micron for zinc oxide and within the range 0.02 to 0.1 micron for titanium dioxide.

The particles to be used in the present invention may be uncoated or coated as is desired with one or more oxides or hydrous oxides of e.g. aluminium, silicon, titanium, zirconium, magnesium or zinc.

One preferred coating which is useful on either the zinc oxide particles or the titanium oxide particles or both is formed of an oxide or hydrous oxide of aluminium and an oxide or hydrous oxide of silicon. When a coating of aluminium oxide and silicon oxide is present on the titanium dioxide particles then it is preferred that the weight ratio $Al_2O_3:SiO_2$ is at least 1.0 and not greater than 4.5, and more preferably the ratio is in the range 1.5 to 3.5. For the zinc oxide particles it is preferred that the coatings contain aluminium and silicon oxides in a weight ratio of $Al_2O_3:SiO_2$ of at least 0.5 and not greater than 4.5 and more preferably the ratio is within the range 0.5 to 3.5.

When such a coating of aluminium and silicon oxides is used then the actual amount of coating present is such that the amount of oxide or hydrous oxide of aluminium when expressed as $Al_2O_3$ is from 1.0 to 30.0 weight per cent based on the weight of solid (zinc oxide and/or titanium dioxide), and preferably from 3.0 to 15.0 weight per cent $Al_2O_3$ on weight of solid (zinc oxide and/or titanium dioxide). Consequently the amount of oxide or hydrous oxide of silicon will be that necessary to maintain the ratio of the amounts of coating oxides or hydrous oxide within the specified range and generally speaking the weight of oxide or hydrous oxide of silicon will be within the range 0.2 to 20.0 weight per cent $SiO_2$ based on solid (zinc oxide and/or titanium dioxide) and preferably from 1.5 to 7.0 weight per cent.

If desired the particulate material may carry a coating of one or more organic material such as an organic silicon compound e.g. a polymeric organic silicon compound. Other organic coating agents which may be present are the polyols, amines or alkanolamines.

The particulate zinc oxide used in the present invention may be formed by any suitable process and typical processes are the French Method in which metallic zinc is melted and evaporated before being oxidized in the gas phase, the American method in which zinc ores are sintered and reduced with cokes and the zinc thus obtained is oxidised to zinc oxide and a wet method in which a water soluble zinc salt such as zinc chloride or zinc sulphate is crystallised and then converted to zinc oxide by sintering.

The titanium dioxide particles may be anatase titanium dioxide, rutile titanium dioxide or amorphous. They may be formed by any suitable process. Typical processes may involve hydrolysis of an appropriate titanium compound such as titanium tetrachloride or an organic or inorganic titanate or oxidation of an oxidisable titanium compound in the vapour state.

In a typical process a titaniferous ore is digested with concentrated sulphuric acid and the digestion cake dissolved in water or dilute acid to produce a titanyl sulphate solution. Hydrolysis of the titanyl sulphate solution produces a precipitate of hydrous titanium dioxide and soluble iron compounds remain in solution. The hydrous titanium dioxide is neutralised and washed to an appropriate degree of impurity level and, if desired, can be treated with sodium hydroxide and subsequently hydrochloric acid to form an acicular titanium dioxide product.

In the process of the invention the particles are milled in an oil until the extinction coefficients E(308) and E(360) as hereinbefore defined reach the values specified. When zinc oxide is used alone then E(308) is greater than 9 liters per gram per centimeter and E(360) is greater than 9 liters per gram per centimeter and preferably greater than 10 liters per gram per centimeter. More preferably both E(308) and E(360) are greater than 12 liters per gram per centimeter and most preferably both E(308) and E(360) are between 12 and 30 liters per gram per centimeter. When a mixed oxide dispersion is formed according to the preferred embodiment of the invention then E(308) for the dispersion is at least 15 liters per gram per centimeter and preferably between 15 and 55 liters per gram per centimeter and E(360) for the dispersion is at least 10 liters per gram per centimeter and preferably between 12 and 25 liters per gram per centimeter.

The ratio E(360):E(308) provides an indication of the relative absorbance of the dispersion prepared in the method of the invention for UVA and UVB light. When zinc oxide is the only particulate material used this ratio is in the range 0.75:1 to 1.5:1 and, preferably, in the range 0.9:1 to 1.2:1. In the preferred method E(360):E(308) for the mixed oxide dispersion is in the range 0.3:1 to 1.5:1 and, preferably, 0.5:1 to 1.2:1.

The oil can be any oil which finds value in a cosmetic sunscreen preparation. Such oils usually are the vegetable oils, for example, fatty acid glycerides, fatty acid esters and fatty alcohols with typical examples being sunflower oil (fatty acid triglyceride), castor oil, oleic and linoleic glycerides, oleyl alcohol, isopropyl palmitate, pentaerythritol tetracaprylate/caprate, propylene glycol dioesters of coconut fatty acids and pentaerythritol tetraisostearate.

The mill which is employed to effect the grinding of the zinc oxide or, in the preferred method, zinc oxide and titanium dioxide in the oil is one which uses a particulate grinding medium to grind the product. Such mills are bead mills equipped with one or more agitators and using sand, glass beads, ceramic beads or other particles as the grinding medium.

Particularly useful are those mills which operate at a high speed and depending on the size of mill a speed of the order of 2500 rev per minute (r.p.m) is not unusual. For instance mills operating at a speed of from 1000 r.p.m. to 6000 r.p.m. are suitable. Agitator mills in which the tip speed of the agitator is up to and can exceed 10 meters/sec are of use. If desired the mill can be cooled. Also the ingredients of the dispersions can be premixed using a high speed stirrer or the oil can be added to the mill initially and then the zinc oxide and/or titanium dioxide and the organic dispersant co-added to the oil subsequently. After milling has been carried out for the required time the dispersion is usually separated from the grinding medium by screening through a narrow gap.

The dispersions prepared in the method of the present invention include an organic dispersing agent to promote the dispersion of the particulate zinc oxide or zinc oxide and titanium dioxide in the chosen oil. Many types of organic dispersing agent have been developed and are available for use in promoting the dispersion of particles in oily media. Typically the dispersing agent can be one having a formula X.CO.AR in which A is a divalent bridging group, R is a primary secondary or tertiary amino group or a salt thereof with an acid or a quaternary ammonium salt group and X is the residue of a polyester chain which together with the —CO— group is derived from a hydroxy carboxylic acid of the formula HO—$R^6$—COOH. As examples of typical dispersing agents are those based on ricinoleic acid, hydroxystearic acid, hydrogenated castor oil fatty acid which contains in addition to 12-hydroxy-stearic acid small amounts of stearic acid and palmitic acid.

Dispersing agents which are polyesters or salts of one or more hydroxycarboxylic acid can also be used. These polyesters may also be formed from hydroxy carboxylic acids and carboxylic acids free from hydroxy groups. Compounds of various molecular weight can be used.

Other suitable dispersing agents are those monoesters of fatty acid alkanolamides and carboxylic acids and their salts based on 6–22 C (un)saturated fatty acids. Alkanolamides are based on ethanolamine, propanolamine or aminoethyl ethanolamine for example. Alternative dispersing agents are those based on polymers or copolymers of acrylic or methacrylic acids e.g. block copolymers of such monomers.

Other dispersing agents of similar general form are those having epoxy groups in the constituent radicals such as those based on the ethoxylated phosphate esters.

The dispersing agent can be one of those commercially referred to as a hyperdispersant specifically available as such and a particularly useful form of hyperdispersant is polyhydroxy stearic acid.

In the preferred method of the invention zinc oxide and titanium dioxide are dispersed. A different dispersing agent can be used for each oxide but it is preferable to use one dispersing agent to disperse both oxides.

Since the products of the method of the invention are to be used in cosmetic or skin care preparations then the ingredients must have an acceptable level of toxicity and irritancy.

The quantity of the dispersing agent used depends on various factors but generally an amount of from 5 per cent to 35 per cent, preferably 5 to 20 per cent by weight based on the weight of particulate material will be used.

The dispersions prepared according to the first stage of the process of this invention provide a convenient form of ultraviolet absorber which is then mixed with one or more cosmetically acceptable materials to prepare various types of cosmetic compositions.

For example foundations are prepared by mixing the dispersion with loading pigment, colouring pigment, oil and shaping agent as desired; creams are prepared by mixing the dispersion with oil, water and emulsifier; lotions are prepared by mixing the dispersion with oil, water, solubilising agent and lower alcohol; lipsticks are prepared by mixing the dispersion with oil and colourant.

Usually, further ingredients such as perfume, anti-oxidant, humectant and corrosion inhibitor are mixed with the emulsion and other ingredients to produce a commercial sunscreen.

Typically, in a general method for preparing a sunscreen a dispersion prepared as described hereinbefore is mixed with an oil phase to form a first phase (Phase A) and a second phase (Phase B) is prepared by mixing water, triethanolamine and a 2% aqueous solution of a copolymer of acrylic acid and a long chain alkyl methacrylate sold as Carbopol 981. Phase A and Phase B are separately heated to 80° C. and Phase A is slowly added to Phase B with stirring. The mixture is cooled with stirring and when the temperature reaches 55° C. it is emulsified by mechanical mixing until smooth and glossy. The emulsified mixture is further cooled to 45° C. with stirring and preservatives are added before final cooling to room temperature with stirring.

The quantities used in any particular sunscreen will depend upon the nature of the sunscreen, and the degree of protection from UV light desired.

The method of the current invention provides a convenient and economical method for the production of a wide variety of sunscreens. In particular the use of a dispersion of zinc oxide or a mixture of zinc oxide and titanium dioxide has been shown to produce a sunscreen having a higher sun protection factor than a similar sunscreen prepared using particulate oxide which has not been dispersed as described in the method of this invention.

The invention is illustrated in the following examples.

EXAMPLE 1

A sample of spherical zinc oxide having an average crystal size of 0.05 microns was dispersed in oil. 175 grams of dry product was added with 249.4 grams of equal parts by weight of a mineral oil sold under the Trade Name Ondina L and a triglyceride of caprylic/caprinic acid sold under the Trade Name Myritol 318 and 13.1 grams of a dispersant being a polyhydroxy stearic acid known as Solsperse 3000 to a high speed bead mill (Eiger M-250-VSE) with 200 g of 1 mm glass beads as a grinding aid. The dispersion was milled for 45 minutes. The solids content of the dispersion was 40% by weight.

After separation from the grinding aid a portion (0.02 g) of the milled dispersion was diluted with cyclohexane (100 ml). The total dilution was 1:5,000.

The diluted sample was then exposed in a spectrometer (Perkin-Elmer Lambda 2) with a 1 cm cell path length and the absorbance of UV and visible light measured. Extinction coefficients at four wavelengths were calculated from the equation $A = E \cdot c \cdot l$ where $A$=absorbance, $E$=Extinction coefficient in liters per gram per cm, $c$=concentration in grams per liter and $l$=path length in cm.

The absorbance of UV and visible light was measured as described above and the extinction coefficients at the four wavelengths calculated were as follows:

| E(308) | E(360) | E(524) | E(max) | λ(max) |
|--------|--------|--------|--------|--------|
| 11.5   | 11.5   | 0.6    | 11.6   | 362 nm |

A sample of the zinc oxide dispersion was made into a sunscreen composition according to the following formulation:

|  | % |
|---|---|
| Oil Phase | |
| Stearic acid | 2.00 |
| Sorbitan monostearate (Glycomul S) | 2.50 |
| Polyoxyethylene (20) sorbitan monostearate (Glycosperse S20) | 3.50 |
| Glycerol fatty acid esters (Teginacid H) | 7.50 |
| Stearyl alcohol and ethoxylates of stearyl alcohol (Emulgator E2155) | 2.50 |
| Alkylated polyvinylpyrrolidone (Antaron V220) | 2.00 |
| Polydimethyl siloxane (Dimethicone 200/350) | 0.50 |
| ZnO dispersion at 40% | 15.00 |
| Mineral Oil/Triglyceride | 1.75 |
|  | 37.25 |
| Aqueous Phase | |
| Demineralised water | 53.14 |
| Triethanolamine (99.9%) | 0.35 |
| Carbopol 981 (2% Solution) | 7.00 |
|  | 60.49 |
| Preservatives | |
| Propylene Glycol | 2.00 |
| Mixed alkyl esters of 4-hydroxybenzoic aicd (Nipastat) | 0.15 |
| Sorbic acid | 0.10 |
| 2-Bromo-2-nitro-1,3-propanediol | 0.01 |
|  | 2.26 |

The sunscreen composition was prepared in a beaker using as agitator a colloid mill (Silverson). The items in the oil phase and the aqueous phase were separately heated to 70° C. The oil phase was then slowly added to the aqueous phase with stirring. When the temperature reached 55° C., it was emulsified by mechanical mixing until smooth and glossy. The emulsified mixture was further cooled to 45° C. with stirring and the preservatives were added before final cooling to room temperature with stirring.

A further sunscreen composition was prepared in a similar manner to the previous one except that 6 pts of zinc oxide powder were used in place of the 15 pts of zinc oxide dispersion and an additional 9 pts (total 10.75 pts) of mineral oil/triglyceride mixture were added to the oil phase.

The compositions were then tested to determine the sun protection factors (SPF) using the in vitro method described in detail by B. L. Diffey and J. Robson (J.Soc. Cosmet. Chem, Vol.40, 127–133, 1989) using a tape substrate (Transpore™ tape, 3M) which has surface irregularities similar to human skin.

Spectroradiometric measurements of the transmission of UV light through the substrate, with and without sunscreen applied, were used to determine the monochromatic protection factors and hence SPF values. The monochromatic protection factors provide information on protection against both ultra-violet B (UVB) radiation (290 nm–320 nm) and longer wavelength ultra-violet A (UVA) radiation (320 nm–400 nm).

The intensity of radiation transmitted through the substrate, with and without sunscreen, is determined automatically by recording photocurrent in 5 nm steps from 290 nm–400 nm.

For the two sunscreen compositions the results were as follows:

|           | ZnO dispersion | ZnO powder |
|-----------|----------------|------------|
| SPF value | 4.5            | 3.0        |

EXAMPLE 2

A dispersion of titanium dioxide in oil was prepared from titanium dioxide whose particles were acicular with an average size of 0.02×0.10 micron and were coated with 5% silica and 10% alumina. 175 grams of this titanium dioxide was added with 245 grams of a mixture of equal parts by weight of a mineral oil sold under the Trade Name Ondina L and a triglyceride of caprylic/caprinic acid sold under the Trade Name Myritol 318 and 17.5 grams of a dispersant being a polyhydroxy stearic acid known as Solsperse 3000 to a high speed bead mill (Eiger M-250-VSE) with 200 grams of 1 mm glass beads as a grinding aid. The dispersion was milled for 45 minutes. The solids content of the dispersion was 40% by weight.

Portions of this titanium dioxide dispersion were mixed by stirring thoroughly with portions of the zinc oxide dispersion used in Example 1 to produce two mixed oxide dispersions, the ratios of zinc oxide:titanium dioxide being 1:1 (Dispersion 2A) and 3:1 (Dispersion 2B) by weight.

The absorbance of the UV and visible light at a dilution of 1:5,000 was measured for each dispersion as described in Example 1 and the extinction coefficients were as follows:

|    | E(308) | E(360) | E(524) | E(max) | λ(max)  |
|----|--------|--------|--------|--------|---------|
| 2A | 24.4   | 16.3   | 4.6    | 25.0   | 298 nm  |
| 2B | 19.3   | 13.2   | 2.1    | 20.0   | 291 nm  |

Sunscreens were prepared from Dispersions 2A and 2B in a manner similar to that described in Example 1. Two further suncreen compositions were also prepared in a manner similar to that described in Example 1, except that in one case (2C), 3 parts of zinc oxide powder and 3 parts of coated titanium dioxide powder were used in place of 15 parts of zinc oxide/titanium dioxide 1:1 dispersion (dispersion 2A), while in the other case (2D) 4.5 parts zinc oxide powder and 1.5 parts titanium dioxide powder were used in place of 15 parts zinc oxide/titanium dioxide 3:1 dispersion (dispersion 2B), both with an additional 9 parts (total 10.75 parts) of mineral oil/triglyceride mixture being added to the oil phase.

It was noticeable that both of the formulations containing powders had a grainy appearance and had an inferior feel to the creams formulated using dispersions. These were then tested as described in Example 1 to determine SPF values which were as follows:

|           | 2A  | 2C  |
|-----------|-----|-----|
| SPF value | 9.8 | 7.4 |

|           | 2B  | 2D  |
|-----------|-----|-----|
| SPF value | 7.7 | 6.7 |

EXAMPLE 3

A dispersion in oil of uncoated zinc oxide powder as used in Example 1 and coated titanium dioxide powder as used in Example 2 was prepared. 87.5 grams of the dry zinc oxide powder and 87.5 grams of the dry titanium dioxide powder were added with 249.4 grams of a mixture of equal parts by weight of a mineral oil sold under the Trade Name Ondina L and a triglyceride of caprylic/caprinic acid and 15.31 grams of a dispersant being a polyhydroxy stearic acid known as Solsperse 3000 to a high speed mill (Eiger M-250-VSE) with 200 grams of 1 mm glass beads as a grinding aid. The dispersion was milled for 45 minutes. The solids content of the dispersion was 40% by weight of solid (20% zinc oxide and 20% titanium dioxide).

After separation from the grinding aid a portion of the milled dispersion was diluted with cyclohexane to a total dilution of 1:5,000 and the absorbance of UV and visible light was measured as described in Example 1. The extinction coefficients at the four wavelengths calculated as follows:

| E(308) | E(360) | E(524) | E(max) | λ(max)  |
|--------|--------|--------|--------|---------|
| 29.0   | 17.3   | 2.9    | 29.3   | 299 nm  |

A sunscreen composition was prepared from the zinc oxide/titanium dioxide co-dispersion using a formulation similar to that given in Example 1 with the zinc oxide dispersion replaced by the mixed oxide dispersion and using the method of Example 1.

The sunscreen was then tested as described in Example 1 to determine the SPF value.

The SPF value was 10.7.

EXAMPLE 4

A further dispersion similar to Example 3 was prepared but using 131.25 grams of dry zinc oxide powder and 43.75 grams of dry coated titanium dioxide, to give a 40% solids dispersion (30% zinc oxide and 10% titanium dioxide).

The absorbance of UV and visible light was measured at a dilution of 1:5,000 as described in Example 1 and the extinction coefficients at the four wavelengths calculated were as follows:

| E(308) | E(360) | E(524) | E(max) | λ(max)  |
|--------|--------|--------|--------|---------|
| 17.6   | 13.1   | 2.1    | 18.7   | 275 nm  |

A sunscreen composition was prepared as described in Example 1. The SPF value was 8.1.

I claim:

1. A method for the preparation of a sunscreen composition containing a zinc oxide dispersion comprising milling a particulate zinc oxide in an oil in the presence of a particulate grinding medium and an organic dispersing agent for said zinc oxide in said oil to form a dispersion, continuing said milling for a period of time such that the particulate zinc oxide has a average size of from 0.005 to 0.15 micron and that the dispersion is substantially transparent to visible light and has an absorbance for ultraviolet light such that the extinction coefficient (E(308)) at a wavelength of 308 nm is at least 9 liters per gram per centimeter, the extinction coefficient (E(360)) at a wavelength of 360 nm is at least 9 liters per gram per centimeter and the ratio E(360):E(308) is in the range 0.75:1 to 1.5:1, separating the particulate grinding medium from the dispersion and mixing the dispersion with one or more cosmetically acceptable materials.

2. A method according to claim 1 in which the ratio E(360):E(308) is in the range 0.9:1 to 1.2:1.

3. A method according to claim 1 in which E(360) is greater than 10 liters per gram per centimeter.

4. A method according to claim 1 in which E(308) and E(360) are each greater than 12 liters per gram per centimeter.

5. A method according to claim 1 in which E(308) and E(360) are between 12 and 30 liters per gram per centimeter.

6. A method for the preparation of a sunscreen composition containing a zinc oxide dispersion comprising milling a particulate zinc oxide and particulate titanium dioxide in an oil in the presence of a particulate grinding medium and an organic dispersing agent for said zinc oxide in said oil and an organic dispersing agent for said titanium dioxide in said oil, continuing said milling for a period of time such that the particulate zinc oxide and the particulate titanium dioxide each have an average size of from 0.005 to 0.15 micron, forming a mixed oxide dispersion, said dispersion being substantially transparent to visible light and having an absorbance for ultraviolet light such that the extinction coefficient (E(308)) at a wavelength of 308 nm is at least 15 liters per gram per centimeter, the extinction coefficient (E(360)) at a wavelength of 360 nm is at least 10 liters per gram per centimeter and the ratio E(360):E(308) is in the range 0.3:1 to 1.5:1, separating the particulate grinding medium from the dispersion and mixing the dispersion with one or more cosmetically acceptable materials.

7. A method according to claim 6 in which the ratio E(360):E(308) is in the range 0.5:1 to 1.2:1.

8. A method according to claim 6 in which E(308) is between 15 and 55 liters per gram per centimeter.

9. A method according to claim 6 in which E(360) is between 12 and 25 liters per gram per centimeter.

10. A method according to claim 6 in which the particles of titanium dioxide are substantially spherical and have an average diameter in the range 0.01 to 0.03 micron.

11. A method according to claim 6 in which the particles of titanium dioxide are acicular with an average largest dimension in the range 0.02 to 0.1 micron.

12. A method according to claim 1 or 6 in which the particles of zinc oxide are substantially spherical and have an average diameter in the range 0.01 to 0.1 micron.

13. A method according to claim 12 in which the average diameter is in the range 0.03 to 0.07 micron.

14. A method according to claim 1 or 6 in which the particles of zinc oxide are acicular and have an average largest dimension in the range 0.05 to 0.12 micron.

15. A method according to claim 1 or 6 in which the particles of zinc oxide or particles of titanium dioxide have a coating comprising one or more oxide or hydrous oxide selected from the group consisting of oxides and hydrous oxides of aluminium, silicon, titanium, zirconium, magnesium and zinc.

16. A method according to claim 15 in which the coating comprises an oxide or hydrous oxide of aluminium and an oxide or hydrous oxide of silicon.

17. A method according to claim 16 in which the coating on the titanium dioxide particles contains aluminium and silicon oxides or hydrous oxides in a weight ratio, calculated as $Al_2O_3:SiO_2$, of at least 1.0 and not more than 4.5.

18. A method according to claim 17 in which the weight ratio is in the range 1.5 to 3.5.

19. A method according to claim 16 in which the coating on the zinc oxide particles contains aluminium and silicon oxides or hydrous oxides in a weight ratio, calculated as $Al_2O_3:SiO_2$, of at least 0.5 and not more than 4.5.

20. A method according to claim 19 in which the weight ratio is in the range 0.5 to 3.5.

21. A method according to claim 16 in which the oxide or hydrous oxide of aluminium is present in an amount of from 1.0 to 30.0 weight per cent, calculated as $Al_2O_3$, based on total weight of zinc oxide and titanium dioxide.

22. A method according to claim 21 in which the amount of oxide or hydrous oxide of aluminium is from 3.0 to 15.0 weight per cent based on total weight of zinc oxide and titanium dioxide.

23. A method according to claim 16 in which the oxide or hydrous oxide of silicon is present in an amount of from 0.2 to 20.0 weight per cent, calculated as $SiO_2$, based on total weight of zinc oxide and titanium dioxide.

24. A method according to claim 23 in which the amount of oxide or hydrous oxide of silicon is from 1.5 to 7.0 per cent by weight based on total weight of zinc oxide and titanium dioxide.

25. A method according to claim 1 or 6 in which the particles of zinc oxide or the particles of titanium dioxide have a coating of an organic material selected from the group consisting of polymeric organic silicon compounds, polyols, amines and alkanolamines.

26. A method according to claim 1 or 6 in which the amount of zinc oxide in the dispersion is at least 30 per cent by weight.

27. A method according to claim 1 or 6 in which the oil is selected from the group consisting of fatty acid glycerides, fatty acid esters and fatty alcohols.

28. A method according to claim 1 or 6 in which the particulate grinding medium is selected from the group consisting of sand, glass beads and ceramic beads.

29. A method according to claim 1 or 6 in which the milling is effected in a mill operating at a speed of from 1000 to 6000 revolutions per minute.

30. A method according to claim 1 or 6 in which the dispersing agent is based on a compound selected from the group consisting of ricinoleic acid, hydroxystearic acid and hydrogenated castor oil fatty acid.

31. A method according to claim 1 or 6 in which the amount of dispersing agent used is from 5 to 35 weight per cent based on total weight of zinc oxide and titanium dioxide.

32. A method according to claim 31 in which the amount of dispersing agent is from 5 to 20 weight per cent.

33. A method according to claim 1 or 6 in which the dispersion is mixed with cosmetically acceptable materials to form an oil phase, an aqueous phase containing an alkanolamine and a polymeric thickener is prepared, the oil phase and the aqueous phase are separately heated to a temperature of approximately 80° C., the phases are mixed with stirring and the resulting mixture is cooled to approximately 55° C. and emulsified by mechanical mixing.

34. The method according to claim 1 or 6 wherein the organic dispersing agent is a polyhydroxy stearic acid.

35. A method according to claim 1 or 6 wherein the cosmetically acceptable materials produce a sunscreen composition selected from the group consisting of an emulsion, a foundation, a cream, a lotion and a lipstick.

* * * * *